US006645476B1

(12) United States Patent
Morschhäuser et al.

(10) Patent No.: US 6,645,476 B1
(45) Date of Patent: Nov. 11, 2003

(54) WATER-SOLUBLE POLYMERS AND THEIR USE IN COSMETIC AND PHARMACEUTICAL COMPOSITIONS

(75) Inventors: Roman Morschhäuser, Mainz (DE); Matthias Löffler, Niedernhausen (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/616,253

(22) Filed: Jul. 14, 2000

(30) Foreign Application Priority Data

Jul. 15, 1999 (DE) ......................... 199 33 066
Jun. 21, 2000 (DE) ......................... 100 29 462

(51) Int. Cl.$^7$ ............... A61K 7/06; A61K 7/08; A61K 9/00; A61K 47/32; A01N 25/00
(52) U.S. Cl. .............. 424/70.1; 424/400; 424/70.21; 514/772.4; 514/937
(58) Field of Search ................. 424/70.1, 400, 424/70.21; 514/772.4, 937; 526/320, 318

(56) References Cited

U.S. PATENT DOCUMENTS

| | | | |
|---|---|---|---|
| 2,809,971 A | 10/1957 | Bernstein et al. | 260/270 |
| 3,236,733 A | 2/1966 | Karsten et al. | 167/87 |
| 3,753,916 A | 8/1973 | Parran, Jr. | 252/107 |
| 3,761,417 A | 9/1973 | Parran, Jr. | 252/106 |
| 3,761,418 A | 9/1973 | Parran, Jr. | 252/106 |
| 4,166,845 A | 9/1979 | Hansen et al. | 424/78 |
| 4,185,106 A | 1/1980 | Dittmar et al. | 424/263 |
| 4,323,683 A | 4/1982 | Bolich, Jr. et al. | 546/6 |
| 4,345,080 A | 8/1982 | Bolich, Jr. | 546/6 |

(List continued on next page.)

FOREIGN PATENT DOCUMENTS

| | | |
|---|---|---|
| EP | 0 285 388 | 10/1988 |
| EP | 0 583 814 | 2/1994 |
| EP | 0 629 649 | 12/1994 |
| EP | 0 850 894 | 7/1998 |
| GB | 1167524 | * 10/1969 |
| GB | 1167524 | 11/1969 |
| GB | 2 084 124 A | 4/1982 |
| WO | WO 94/24204 | 11/1994 |
| WO | WO 97/14448 | 4/1997 |

OTHER PUBLICATIONS

Barbar et al., In–Vitro Release of Zinc Pyrethhione From A Shampoo Base And The Effect of Various Additives On Its Release Rate, Drug Development and Industrial Pharmacy, 11(8), 1507–1522 (1985).
R.L. Goldemberg, Advances in Cosmetic Technology, vol. 1, pp. 70–71 (1978).

Primary Examiner—Thurman K. Page
Assistant Examiner—Blessing Fubara
(74) Attorney, Agent, or Firm—Susan B. Jackson; Richard P. Silverman (57) ABSTRACT

The invention provides water-soluble polymers preparable by free-radical copolymerization of A) one or more macromonomers containing an end-group capable of polymerization, a hydrophilic moiety based on polyalkylene oxides, and a hydrophobic moiety which comprises hydrogen or a saturated or unsaturated, linear or branched, aliphatic, cycloaliphatic or aromatic ($C_1$–$C_{30}$)-hydrocarbon radical, and B) one or more olefinically unsaturated comonomers which contain oxygen, nitrogen, sulfur, phosphorus, chlorine and/or fluorine. The polymers are suitable as thickeners, dispersing agents, emulsifiers, suspending agents, stabilizers and/or bodying agents for aqueous preparations, emulsions and suspensions, in particular for cosmetic and pharmaceutical compositions.

76 Claims, 3 Drawing Sheets

U.S. PATENT DOCUMENTS

| | | | |
|---|---|---|---|
| 4,379,753 A | 4/1983 | Bolich, Jr. | 252/106 |
| 4,405,645 A | 9/1983 | Röthlisberger et al. | 424/326 |
| 4,470,982 A | 9/1984 | Winkler | 424/245 |
| 4,492,646 A | 1/1985 | Welch | 252/528 |
| 4,557,928 A | 12/1985 | Glover | 424/70 |
| 4,559,227 A | 12/1985 | Chandra et al. | 424/70 |
| 4,631,187 A | 12/1986 | Padden et al. | 424/70 |
| 4,711,775 A | 12/1987 | Dittmar et al. | 424/70 |
| 4,801,447 A | 1/1989 | Gum | 424/68 |
| 4,898,725 A | 2/1990 | Hoeffkes et al. | 424/70 |
| 4,935,224 A | 6/1990 | Russo et al. | 424/47 |
| 5,045,619 A | 9/1991 | Kuroda et al. | |
| 5,086,142 A * | 2/1992 | Fock et al. | 526/318 |
| 5,104,645 A | 4/1992 | Cardin et al. | 424/70 |
| 5,395,907 A * | 3/1995 | Zajaczkowski | 526/320 |
| 5,480,953 A | 1/1996 | Sugaya et al. | |
| 5,491,209 A | 2/1996 | Helmer et al. | 526/320 |
| 5,508,367 A | 4/1996 | Zajaczkowski | 526/320 |
| 5,565,268 A | 10/1996 | Zajaczkowski | 428/355 |
| 5,712,359 A | 1/1998 | Auschra et al. | |
| 5,726,250 A | 3/1998 | Zajaczkowski | 525/296 |
| 5,731,387 A | 3/1998 | Zajaczkowski | 525/330.2 |
| 5,837,789 A | 11/1998 | Stockhausen et al. | |
| 5,849,840 A | 12/1998 | Maruhashi et al. | |
| 5,912,284 A | 6/1999 | Hirata et al. | 524/5 |

* cited by examiner

WATER-SOLUBLE POLYMERS AND THEIR USE IN COSMETIC AND PHARMACEUTICAL COMPOSITIONS

BACKGROUND OF THE INVENTION

The present invention relates to water-soluble polymers prepared by copolymerization of macromonomers, and to their use in cosmetic and pharmaceutical compositions.

In recent years water-soluble polymers have achieved ever increasing importance in industry and science. In terms of quantity, polyelectrolytes make up a very large part of the overall annual production of water-soluble polymers. They are used as flocculants in paper processing, the detergents industry, textile processing, as protective colloids or, in their crosslinked variants, as thickeners, to name but a few areas of application.

The hygiene sector has become hard to imagine without thickeners, in particular the "superabsorbents" prepared on the basis of polyacrylic acid, since their development in the 1970s. Newer thickeners, such as, for example, crosslinked polyacrylamidopropylenemethylsulfonic acid (or salts thereof), are notable for their significantly improved pH stability and better processability.

With the aim of simplifying cosmetic preparations, the search has intensified in recent years for raw materials which combine two or more properties in one formulation constituent. Pure "thickeners" have been replaced by new substances which, in their property profile, also have emulsifier properties, for example, thus rendering the addition of separate emulsifiers in formulations unnecessary. The synthesis of the polymers described below offers the ideal instrument for this purpose. The interesting combination of a polyelectrolyte (e.g. poly-AMPS) with nonpolar molecular moieties offers the possibility of varying the hydrophilic-hydrophobic balance of a polymer, as has hitherto only been observed in synthetic polymer chemistry in a few cases.

The temperature behavior of the polymers is an important property. Generally, polymers display high viscosity at low temperatures, and low viscosity at high temperatures. However, polymers which have a thickening action above certain temperatures, but remain pumpable and processable in solution at low temperatures, are frequently desired.

EP-A-0 583 814 and EP-A-0 629 649 disclose polymers based on acrylic acid as the main chain and polyethylene and/or polypropylene glycols as side chains. These polymers display thickening at increasing temperatures.

All attempts to produce such polymers on an industrial scale have hitherto been unsuccessful. In addition, the use of acrylic-acid-containing main chain polymers was necessary for realizing the concept of thermothickening polymer solutions in water. One of the most serious problems for this class of polymer are precipitation phenomena based on instabilities toward divalent ions.

SUMMARY OF THE INVENTION

In the present invention, then, a novel class of polymer and a process for the preparation thereof are described. Without great preparation costs, using this process based on a free-radical copolymerization, in particular precipitation polymerization, it is possible to prepare a large number of novel polymers with different thermal solution behavior on an industrial scale.

Surprisingly, we have found that polymers which satisfy said requirements can also be synthesized by means of a macromonomer synthesis. The consequence of this is that the stipulation for acrylic acid as one of the main chain monomers, which is required in accordance with the prior art, is unnecessary.

DESCRIPTION OF THE PREFERRED EMBODIMENTS

The invention provides water-soluble polymers preparable by free-radical copolymerization of A) one or more macromonomers containing an end-group capable of polymerization, a hydrophilic moiety based on polyalkylene oxides, and a hydrophobic moiety which comprises hydrogen or a saturated or unsaturated, linear or branched, aliphatic, cycloaliphatic or aromatic $(C_1-C_{30})$-hydrocarbon radical, and B) one or more olefinically unsaturated comonomers which contain oxygen, nitrogen, sulfur, phosphorus, chlorine and/or fluorine.

The macromonomers A) are preferably those of the formula (1)

$$R^1-Y-(R^2-O)_x-R^3 \qquad (1)$$

in which $R^1$ is a vinyl, allyl, acrylic or methacrylic radical; $R^2$ is $(C_2-C_4)$-alkylene; x is an integer between 1 and 500; Y=O, S, PH or NH; and $R^3$ is hydrogen or a saturated or unsaturated linear or branched aliphatic, cycloaliphatic or aromatic $(C_1-C_{30})$-hydrocarbon radical.

$R^1$ is particularly preferably an acrylic or methacrylic radical; $R^2$ is particularly preferably an ethylene or propylene radical; x is particularly preferably a number between 3 and 50, especially preferably a number between 7 and 30. $R^3$ is preferably an aliphatic or cycloaliphatic hydrocarbon which may be saturated or unsaturated. $R^3$ is particularly preferably a $(C_6-C_{22})$-hydrocarbon radical, especially preferably a $(C_{12}-C_{18})$-hydrocarbon radical.

The macromonomers are generally prepared by reacting reactive derivatives of (meth)acrylic acid with compounds containing hydroxyl groups, in particular alkoxylated alkyl radicals. The ring-opening addition to (meth)acrylic glycidyl esters is also possible.

Suitable olefinically unsaturated comonomers B) are preferably olefinically unsaturated acids and salts thereof containing mono- and divalent counterions, particularly preferably styrenesulfonic acid, acrylamidopropylmethylenesulfonic acid (AMPS), vinylsulfonic acid, vinylphosphonic acid, allylsulfonic acid, methallylsulfonic acid, (meth)acrylic acid, maleic acid or maleic anhydride and salts thereof; esters of (meth)acrylic acid wilt aliphatic, aromatic or cycloaliphatic alcohols having a carbon number from 1 to 22; esters of (meth)acrylic acid with alkyl ethoxylates, open-chain and cyclic N-vinylamides (N-vinyllactam) having a ring size of from 4 to 9 atoms, particularly preferably N-vinylformamide (NVF), N-vinylmethylformamide, N-vinylmethylacetamide (VIMA), N-vinylacetamide, N-vinylpyrrolidone (NVP) and N-vinylcaprolactam; amides of acrylic acid and of methacrylic acid, particularly preferably acrylamide, N,N- dimethylacrylamide, N,N-diethylacrylamide, alkoxylated acrylamides and methacrylamides, such as, for example methacryloyl propyl trimethyl ammonium chloride (MAPTAC) and acryloyl propyl trimethyl ammonium chloride (APTAC); 2-vinylpyridine; 4-vinylpyridine; vinyl acetate; glycidyl methhacrylate; acrylonitrile; vinyl chloride; vinylidene chloride; tetrafluoroethylene and/or DADMAC.

Suitable counterions for the salts of the olefinically unsaturated acids are preferably lithium, sodium, potassium, magnesium, calcium, ammonium, monoalkylammonium, dialkylammonium, trialkylammonium or tetraalkylammonium, where the alkyl substituents of the ammonium ions are, independently of one another, ($C_1$–$C_{22}$)-alkyl radicals, which can be occupied by 0 to 3 hydroxyalkyl groups whose alkyl chain length can vary in a range from $C_2$ to $C_{10}$. Likewise suitable are mono- to triethoxylated ammonium compounds having a varying degree of ethoxylation. Particularly preferred counterions are sodium and ammonium. The degree of neutralization of the olefinically unsaturated acids is preferably between 70 and 100 mol %.

Particular preference is given to water-soluble polymers preparable by free-radical copolymerization of A) one or more macromonomers chosen from the group of esters of (meth)acrylic acid with alkyl ethoxylates which include 5 to 80 EO units and/or ($C_{10}$–$C_{22}$)-alkyl radicals, and B) one or more olefinically unsaturated comonomers chosen from the group consisting of acrylamidopropylmethylenesulfonic acid (AMPS), sodium and ammonium salts of acrylamidopropylmethylenesulfonic acid (AMPS), acrylamide, N-vinylformamide, N-vinylmethylacetamide and/or sodium methallylsulfonate.

Suitable macromonomers A) in this connection are, in particular, esters of (meth)acrylic acid with ($C_{10}$–$C_{18}$)-fatty alcohol polyglycol ethers with 8 ethylene oxide (EO) units (Genapol® C-080)

$C_{11}$-oxo alcohol polyglycol ethers with 8 ethylene oxide (EO) units (Genapol® UD-080)

($C_{12}$–$C_{14}$)-fatty alcohol polyglycol ethers with 7 ethylene oxide (EO) units (Genapol® LA-070)

($C_{12}$–$C_{14}$)-fatty alcohol polyglycol ethers with 11 ethylene oxide (EO) units (Genapol® LA-110)

($C_{16}$–$C_{18}$)-fatty alcohol polyglycol ethers with 8 ethylene oxide (EO) units (Genapol® T-080)

($C_{16}$–$C_{18}$)-fatty alcohol polyglycol ethers with 15 ethylene oxide (EO) units (Genapol® T-150)

($C_{16}$–$C_{18}$)-fatty alcohol polyglycol ethers with 11 ethylene oxide (EO) units (Genapol® T-110)

($C_{16}$–$C_{18}$)-fatty alcohol polyglycol ethers with 20 ethylene oxide (EO) units (Genapol® T-200)

($C_{16}$–$C_{18}$)-fatty alcohol polyglycol ethers with 25 ethylene oxide (EO) units (Genapol® T-250)

($C_{18}$–$C_{22}$)-fatty alcohol polyglycol ethers with 25 ethylene oxide (EO) units and/or iso($C_{16}$–$C_{18}$)-fatty alcohol polyglycol ethers with 25 ethylene oxide (EO) units and particularly suitable olefinically unsaturated comonomers B) are the sodium and ammonium salts of acrylamidopropylmethylenesulfonic acid (AMPS). The Genapol® grades are products from clariant.

The molar proportions of the macromonomers A) and of the comonomers B) in the polymer can vary between 0.1 and 99.9 mol %.

In a preferred embodiment (polymers modified to have a high degree of hydrophobicity), the proportion of macromonomers A) is 50.1 to 99.9 mol %, preferably 70 to 95 mol %, particularly preferably 80 to 90 mol %. In a further preferred embodiment (polymers modified to have a low degree of hydrophobicity), the proportion of macromonomers A) is 0.1 to 50 mol %, preferably 5 to 25 mol %, particularly preferably 10 to 20 mol %.

The monomer distribution of the macromonomers A) and comonomers B) in the polymers can, for example, be alternating, block-like (including multiblock), or random (including gradient). The polymers generally have a number-average molecular weight of from 1000 to 20,000,000 g/mol, preferably 20,000 to 5,000,000, particularly preferably 100,000 to 1,500,000 g/mol.

In a preferred embodiment, the polymers according to the invention are crosslinked, i.e. they contain at least one crosslinker having at least two double bonds, which is copolymerized into the polymer. Suitable crosslinkers are, in particular, methylenebisacrylamide and methylenebismethacrylamide, esters of unsaturated mono- or polycarboxylic acids with polyols, e.g. diacrylates or triacrylates, such as, for example, butanediol and ethylene glycol diacrylate or methacrylate and trimethylolpropane triacrylate, allyl compounds, such as, for example, allyl (meth)acrylate, triallyl cyanurate, diallyl maleate, polyallyl ester, tetraallyloxyethane, triallylamine, tetraallylethylenediamine, allyl esters of phosphoric acid and/or vinylphosphonic acid derivatives.

A preferred embodiment of the invention relates to polymers which consist of a water-soluble polymer skeleton and macromonomers A) having heat-sensitive side chains, which have LCST behavior in water, and the aqueous solution of which has a viscosity which, above a certain threshold temperature, increases or remains roughly constant with increasing temperature.

A further preferred embodiment of the invention relates to those polymers whose aqueous solution has a viscosity which, below a first threshold temperature, is low, above this first threshold temperature increases to a maximum with increasing temperature, and above a second threshold temperature decreases again with increasing temperature. In this connection, it is preferred that the viscosity of the polymer solutions below the first threshold temperature is 5 to 50%, in particular 10 to 30%, of the maximum viscosity at the second threshold temperature.

A likewise preferred embodiment of the invention represents those polymers whose aqueous solutions, even at room temperature, have a high viscosity and do not have thermoassociative behavior.

The viscosities of the 1% strength aqueous solutions are preferably from 20,000 mPas to 100,000 mpas, in particular 60,000 mPas to 70,000 mpas. Even at room temperature, such polymers exhibit high thickener performance, good emulsifying properties and good dispersion properties in aqueous, aqueous-alcoholic and aqueous/surface-active solution or in emulsions. Furthermore, preparations comprising such polymers exhibit good transparency and high electrolyte stability.

The polymers according to the invention are prepared by free-radical copolymerization, such as, for example, precipitation polymerization, emulsion polymerization, solution polymerization or suspension polymerization. Preference is given to precipitation polymerization, particular preference to precipitation polymerization in tert-butanol.

Using precipitation polymerization in tert-butanol, it is possible to achieve a particle size distribution for the polymer which is particularly favorable for the use of the polymers. The size distribution of the polymer particles can be determined, for example, by laser diffraction or screen analysis. A representative favorable size distribution is the following particle size distribution, as was determined by screen analysis for an AMPS copolymer: 60.2% smaller than 423 micrometers, 52.0% smaller than 212 micrometers, 26.6% smaller than 106 micrometers, 2.6% smaller than 45 micrometers and 26.6% larger than 850 micrometers.

The polymerization reaction can be carried out in the temperature range between 0° C. and 150° C., preferably between 10° C. and 100° C., either at atmospheric pressure or under increased or reduced pressure. As is customary, the polymerization can also be carried out in a protective gas atmosphere, preferably under nitrogen.

To initiate the polymerization, high-energy electromagnetic rays or the customary chemical polymerization initiators can be used, e.g. organic peroxides, such as benzoyl peroxide, tert-butyl hydroperoxide, methyl ethyl ketone peroxide, cumene hydroperoxide, azo compounds, such as, for example, azobisisobutyronitrile, azobisdimethylvaleronitrile, and inorganic peroxy compounds, such as, for example, $(NH_4)_2S_2O_8$, $K_2S_2O_8$ or $H_2O_2$ optionally in combination with reducing agents, such for example, sodium hydrogensulfite and iron(II) sulfate or redox systems which comprise, as reducing component, an aliphatic or aromatic sulfonic acid, such as, for example, benzenesulfonic acid and toluenesulfonic acid or derivatives of these acids such as, for example, Mannich adducts of sulfinic acid, aldehydes and amino compounds.

The polymers according to the invention are suitable as thickeners and dispersing agents for aqueous preparations, aqueous-alcoholic and aqueous/surface-active preparations, and as emulsifiers, suspending agents having a thickening action and bodying agents for emulsions and suspensions. In this connection, it is also possible to use mixtures of the polymers. In particular, the polymers are suitable for use in cosmetic and pharmaceutical compositions. In this connection, it is important that the polymers can be used without co-use of an additional coemulsifier and/or without co-use of an additional bodying agent. The co-use of coemulsifiers and bodying agents is therefore not obligatory, but possible.

The invention thus also provides aqueous preparations, aqueous-alcoholic preparations, aqueous/surface-active preparations, emulsions and suspensions comprising the polymers according to the invention.

The preparations, emulsions and suspensions are preferably cosmetic or pharmaceutical compositions, such as, for example, shampoos, shower preparations, shower gels, foam baths, gels, lotions, creams and ointments.

The preparations, emulsions and suspensions according to the invention comprise, based on the finished formulation, preferably 0.05 to 10% by weight, particularly preferably 0.1 to 5% by weight, especially preferably 0.5 to 3% by weight, of polymers according to the invention.

The polymers according to the invention can be used as thickeners for water-based or water-alcohol-based compositions, for example hair gels. Furthermore, the polymers according to the invention are suitable as thickeners, dispersing agents and bodying agents for aqueous/surface-active preparations, for example shampoos, shower preparations, shower gels, foam baths and the like. The thickening action of the polymers according to the invention in aqueous/surface-active compositions is intensified by an association of the polymer side chains and the surfactants, and can be controlled by the choice of polymer side chains and by the choice of surfactants. The suspending or dispersing and stabilizing action of the polymers according to the invention in aqueous/surface-active compositions is determined by the association of the polymer side chains and of the liquid components insoluble in aqueous/surface-active compositions, for example silicone oils, or the insoluble components, for example zinc pyrethione.

The compositions according to the invention can comprise, as further auxiliaries and additives, all customary anionic, cationic, zwitterionic, nonionic and amphoteric surfactants, and further additives customary in cosmetics, such as, for example, superfatting agents, stabilizers, biogenic active ingredients, glycerol, preservatives, pearlizing agents, dyes and fragrances, solvents, opacifiers, further thickeners and dispersing agents, further protein derivatives, such as gelatin, collagen hydrolysates, natural- and synthetic-based polypeptides, egg yolk, lecithin, lanolin and lanolin derivatives, fatty alcohols, silicones, deodorizing agents, substances having keratolytic and keratoplastic action, enzymes and carrier substances. Furthermore, antimicrobially effective agents can be added to the compositions according to the invention.

The total amount of the surfactants used in the compositions according to the invention can, based on the finished composition, be between 5 and 70% by weight, preferably between 10 and 40% by weight, particularly preferably between 12 and 35% by weight. Anionic detersive substances which may be mentioned are: $(C_{10}-C_{20})$-alkyl and alkylene carboxylates, alkyl ether carboxylates, fatty alcohol sulfates, fatty alcohol ether sulfates, alkylamide sulfates and sulfonates, fatty acid alkylamide polyglycol ether sulfates, alkanesulfonates and hydroxyalkanesulfonates, olefinsulfonates, acyl esters of isethionates, α-sulfo fatty acid esters, alkylbenzene-sulfonates, alkylphenol glycol ether sulfonates, sulfosuccinates, sulfosuccinic monoesters and diesters, fatty alcohol ether phosphates, protein-fatty acid condensation products, alkylmonoglyceride sulfates and sulfonates, alkylglyceride ether sulfonates, fatty acid methyltaurides, fatty acid sarcosinates, sulforicinoleates, acyl glutamates. These compounds and mixtures thereof are used in the form of their water-soluble or water-dispersible salts, for example the sodium, potassium, magnesium, ammonium, mono-, di- and triethanolammonium and analogous alkylammonium salts.

The proportion by weight of the anionic surfactants in the compositions according to the invention is preferably in the range from 7 to 30% by weight, particularly preferably 10 to 25% by weight, especially preferably 12 to 22% by weight.

Suitable cationic surfactants are, for example, quaternary ammonium salts, such as di$(C_{10}-C_{24})$-alkyldimethylammonium chloride or bromide, preferably di$(C_{12}-C_{18})$-alkyldimethylammonium chloride or bromide; $(C_{10}-C_{24})$-alkyldimethylethylammonium chloride or bromide; $(C_{10}-C_{24})$-alkyltrimethylammonium chloride or bromide, preferably cetyltrimethylammonium chloride or bromide and $(C_{20}-C_{22})$-alkyltrimethylammonium chloride or bromide; $(C_{10}-C_{24})$-alkyldimethyl-benzylammonium chloride or bromide, preferably $(C_{12}-C_{18})$-alkyldimethyl-benzylammonium chloride; N-$(C_{10}-C_18)$-alkylpyridinium chloride or bromide, preferably N-$(C_{12}-C_{16})$-alkylpyridinium chloride or bromide; N-$(C_{10}-C_{18})$-alkylisoquinolinium chloride, bromide or monoalkylsulfate; N-$(C_{12}-C_{18})$-alkylpolyolaminoformylmethylpyridinium chloride; N-$(C_{12}-C_{18})$-alkyl-N-methylmorpholinium chloride, bromide or monoalkylsulfate; N-$(C_{12}-C_{18})$-alkyl-N-ethyl-morpholinium chloride, bromide or monoalkylsulfate; $(C_{16}-C_{18})$-alkylpentaoxethylammonium chloride;

diisobutylphenoxyethoxyethyl-dimethylbenzylammonium chloride; salts of N,N-diethylaminoethylstearylamide and oleylamide with hydrochloric acid, acetic acid, lactic acid, citric acid, phosphoric acid; N-acylaminoethyl-N,N-diethyl-N-methylammonium chloride, bromide or monoalkylsulfate and N-acylaminoethyl-N,N-diethyl-N-benzylammonium chloride, bromide or monoalkylsulfate, where acyl is preferably stearyl or oleyl.

The proportion by weight of the cationic surfactants in the compositions according to the invention is preferably in the range from 1 to 10% by weight, particularly preferably 2 to 7% by weight, especially particularly preferably 3 to 5% by weight.

Examples of suitable nonionic surfactants which can be used as detersive substances are: fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acylpolyethylene glycols); polypropylene glycol ethoxylates (Pluronics®); fatty acid alkylolamides (fatty acid amide polyethylene glycols); N-alkyl, N-alkoxypolyhydroxy fatty acid amides, sucrose esters; sorbitol esters and polyglycol ethers.

The proportion by weight of the nonionic surfactants in the compositions according to the invention is preferably in the range from 1 to 20% by weight, particularly preferably 2 to 10% by weight, especially preferably 3 to 7% by weight.

Preferred amphoteric surfactants are: N-($C_{12}$–$C_{18}$)-alkyl-β-aminopropionates and N-($C_{12}$–$C_{18}$)-alkyl-β-iminodipropionates as alkali metal and mono-, di- and trialkylammonium salts; N-acylaminoalkyl-N,N-dimethylacetobetaine, preferably N-($C_8$–$C_{18}$)-acylaminopropyl-N,N-dimethylacetobetaine; ($C_{12}$–$_{18}$)-alkyldimethylsulfopropylbetaine; amphoteric surfactants based on imidazoline (trade name: Miranol®, Steinapon®), preferably the sodium salt of 1-(β-carboxymethyloxyethyl)-1-(carboxymethyl)-2-laurylimidazolinium; amine oxides, e.g. ($C_{12}$–$C_{18}$)-alkyldimethylamine oxide, fatty acid amidoalkyldimethylamine oxide.

The proportion by weight of the amphoteric surfactants in the compositions according to the invention is preferably in the range from 0.5 to 20% by weight, particularly preferably 1 to 10% by weight.

Furthermore, foam-enhancing cosurfactants from the group of alkylbetaines, alkylamidobetaines, aminopropionates, aminoglycinates, imidazoliniumbetaines and sulfobetaines, amine oxides and fatty acid alkanolamides or polyhydroxyamides can be used in the compositions according to the invention.

Preferred surfactants in the compositions according to the invention are lauryl sulfate, laureth sulfate, cocoamidopropylbetaine, sodium cocoyl glutamate, disodium laureth sulfosuccinate and coconut fatty acid diethanolamide.

The preparations according to the invention can additionally comprise further additives customary in cosmetics, such as superfatting agents, stabilizers, biogenic active ingredients, glycerol, preservatives, pearlizing agents, dyes and fragrances, solvents, opacifiers, thickeners and dispersing agents, and also protein derivatives, such as gelatin, collagen hydrolysates, natural- and synthetic-based polypeptides, egg yolk, lecithin, lanolin and lanolin derivatives, fatty alcohols, silicones, deodorizing agents, substances having a keratolytic and keratoplastic action, enzymes and carrier substances. Furthermore, antimicrobially effective agents can be added to the compositions according to the invention.

The superfatting agents used may be substances such as, for example, polyethoxylated lanolin derivatives, lecithin derivatives, polyol fatty acid esters, monoglycerides and fatty acid alkanolamides, the latter also serving as foam stabilizers. Typical examples of fats are glycerides, and suitable waxes are inter alia beeswax, paraffin wax or microcrystalline waxes, optionally in combination with hydrophilic waxes, e.g. cetylstearyl alcohol.

Stabilizers which can be used are metal salts of fatty acids, such as, for example, magnesium, aluminum and/or zinc stearate.

The term biogenic active ingredients means, for example, plant extracts and vitamin complexes.

Suitable preservatives are, for example, phenoxyethanol, formaldehyde solution, parabens, pentanediol or sorbic acid.

Suitable pearlizing agents are, for example, glycol distearic esters, such as ethylene glycol distearate, but also fatty acid monoglycol esters. The dyes which can be used are the substances approved and suitable for cosmetic purposes.

Suitable as further thickeners are sodium chloride, potassium chloride, ammonium chloride, sodium sulfate, fatty acid alkylolamides, cellulose derivatives, for example hydroxyethylcellulose, guar gum, polyvinyl alcohol, polyvinylpyrrolidone, hydroxypropyl guar gum, starch and starch derivatives, and natural gums, carboxyvinyl polymers, for example Carbopol 934, 940, 941, 956, 980, 981, 1342, 1382, ethylene glycol esters of fatty acids having 14 to 22 carbon atoms, particularly preferably 16 to 22 carbon atoms, in particular mono- and diethylene glycol stearate. Preference is also given to stearin monoethanolamide, stearin diethanolamide, stearin isopropanolamide, stearin monoethanolamide stearate, stearyl stearate, cetyl palmitate, glycerol stearate, stearamide diethanolamide distearate, stearamide monoethanolamide stearate, N,N-dihydrocarbyl-($C_{12}$–$C_{22}$)—, in particular $C_{16}$–$C_{18}$)—, amidobenzoic acid and soluble salts thereof, N,N-di($C_{16}$–$C_{18}$)-amidobenzoic acid and derivatives thereof.

The dispersing agents are used, based on the finished composition, in concentrations of from preferably 0.5 to 10% by weight, particularly preferably from 0.5 to 5% by weight, especially preferably from 1 to 4% by weight.

The desired viscosity of the compositions can be adjusted by adding water and/or organic solvents or by adding a combination of organic solvents and thickeners.

In principle, suitable organic solvents are all mono- or polyhydric alcohols. Preference is given to using alcohols having 1 to 4 carbon atoms, such as ethanol, propanol, isopropanol, n-butanol, isobutanol, t-butanol, glycerol and mixtures of said alcohols. Further preferred alcohols are polyethylene glycols having a relative molecular mass below 2000. In particular, a use of polyethylene glycol having a relative molecular mass between 200 and 600 and in amounts of up to 45% by weight, and of polyethylene glycol having a relative molecular mass between 400 and 600 in amounts of from 5 to 25% by weight is preferred. Further suitable solvents are, for example, triacetin (glycerol triacetate) and 1-methoxy-2-propanol.

Suitable carrier materials are vegetable oils, natural and hydrogenated oils, waxes, fats, water, alcohols, polyols, glycerol, glycerides, liquid paraffins, liquid fatty alcohols, sterol, polyethylene glycols, cellulose and cellulose derivatives.

Fungicidal active ingredients which may be used are ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine.

Silicones, polyalkylsiloxanes, polyalkylarylsiloxanes, polyether siloxane copolymers, as described in U.S. Pat. No. 5,104,645 and the publications cited therein, further improve the care action of the compositions according to the invention. The compositions according to the invention can be mixed with conventional ceramides, pseudoceramides, fatty acid N-alkylpolyhydroxyalkylamides, cholesterol, cholesterol fatty acid esters, fatty acids, triglycerides, cerebrosides, phospholipids and similar substances.

The polymers according to the invention can be used as emulsifiers, stabilizers and/or bodying agents in emulsions. In particular, crosslinked polymers are suitable for this purpose. The emulsions can either be water-in-oil emulsions or oil-in-water emulsions.

The emulsifying, stabilizing and/or bodying action of the polymers according to the invention in emulsions is caused or intensified by an association of the polymer side chains with one another, and by interaction of the polymer side chains with the hydrophobic oil components.

The nonaqueous proportion of the emulsions, which is composed largely of the emulsifier, the thickener and the oil substance, is usually 5 to 95% and preferably 15 to 75% by weight. This means that the emulsions may comprise 5 to 95% by weight and preferably 25 to 85% by weight of water, depending on whether the intention is to prepare lotions with relatively low viscosity, or creams and ointments with high viscosity.

The emulsions can be used as skincare compositions, such as, for example, daycreams, nightcreams, care creams, nourishing cream, body lotions, ointments and the like, and, as further auxiliaries and additives, comprise oil substances, coemulsifiers, superfatting agents, fats, waxes, stabilizers, biogenic active ingredients, glycerol, preservatives, dyes and fragrances.

Suitable oil substances are, for example, Guerbet alcohols based on fatty alcohols having 6 to 18, preferably 8 to 10, carbon atoms, esters of linear ($C_6$–$C_{13}$)-fatty acids with linear ($C_6$–$C_{20}$)-fatty alcohols, esters of branched ($C_6$–$C_{13}$)-carboxylic acids with linear ($C_6$–$C_{20}$)-fatty alcohols, esters of linear ($C_6$–$C_{18}$)-fatty acids with branched alcohols, in particular 2-ethylhexanol, esters of linear and/or branched fatty acids with polyhydric alcohols (such as, for example, dimerdiol or trimerdiol) and/or Guerbet alcohols, triglycerides based on ($C_6$–$C_{10}$)-fatty acids, vegetable oils, branched primary alcohols, substituted cyclohexanes, Guerbet carbonates, dialkyl ethers and/or aliphatic or aromatic hydrocarbons. The proportion of the oil substances in the nonaqueous proportion of the emulsions can constitute 5 to 95% by weight and preferably 15 to 75% by weight.

Suitable nonionogenic co-emulsifiers include addition products of from 0 to 30 mol of ethylene oxide and/or 0 to 5 mol of propylene oxide with linear fatty alcohols having 8 to 22 carbon atoms, with fatty acids having 12 to 22 carbon atoms, with alkylphenols having 8 to 15 carbon atoms in the alkyl group, and with sorbitan or sorbitol esters; ($C_{12}$–$C_{18}$)-fatty acid mono- and diesters of addition products of from 0 to 30 mol of ethylene oxide with glycerol; glycerol mono- and diesters and sorbitan mono- and diesters of saturated and unsaturated fatty acids having 6 to 22 carbon atoms and optionally the ethylene oxide addition products thereof; addition products of from 15 to 60 mol of ethylene oxide with castor oil and/or hydrogenated castor oil; polyol and, in particular, polyglycerol esters, such as, for example, polyglycerol polyricinoleate and polyglycerol poly-12-hydroxystearate. Also suitable are mixtures of compounds from two or more of these classes of substance.

Suitable ionogenic co-emulsifiers are, for example, anionic emulsifiers, such as phosphoric mono-, di- or triesters, but also cationic emulsifiers, such as mono-, di- and trialkyl quats and polymeric derivatives thereof.

To adjust the rheological properties of aqueous or solvent-containing emulsions or suspensions, a large number of different systems are given in the specialist literature. Known examples are cellulose ethers and other cellulose derivatives (e.g. carboxymethylcellulose, hydroxyethylcellulose), gelatin, starch and starch derivatives, sodium alginates, fatty acid polyethylene glycol esters, agaragar, tragacanth or dextrins. The synthetic polymers used are a variety of materials such as, for example, polyvinyl alcohols, polyacrylamides, polyvinylamides, polysulfonic acids, polyacrylic acid, polyacrylic esters, polyvinylpyrrolidone, polyvinyl methyl ether, polyethylene oxides, copolymers of maleic anhydride and vinyl methyl ether, and diverse mixtures and copolymers of said compounds, including their various salts and esters. These polymers can be crosslinked or uncrosslinked as desired. The emulsions can be prepared in a known manner, i.e. for example by hot, hot/cold or PIT emulsification.

The polymers according to the invention can also be used for the formulation of crop protection agents. In this area of application, recent years have seen a rethink in the development of new active ingredient formulations. It is not the search for new active ingredients which has been at the forefront, but the search for auxiliary reagents for enhancing the effectiveness of known active ingredients on the surface of crops. The addition of these adjuvants, permits the reduction in the amount of active ingredient used while retaining the effectiveness of the overall formulation compared with adjuvant-free formulations. Water-soluble polyelectrolytes modified so as to be nonpolar on the one hand permit an increase in the viscosity of the active ingredient solution present, which leads to slower "repellency" from leaf surfaces and thus to a prolonged contact time on the leaf, and on the other hand, the nonpolar side radicals effect increased adsorption at the likewise nonpolar surfaces of the leaf.

The examples and applications below serve to illustrate the invention in more detail without, however, limiting it thereto.

EXAMPLES

Examples and Applications

1) Preparation of the Macromonomers a) Variant 1: Glycidyl Methacrylate

A one-liter three-necked flask fitted with stirrer, internal thermometer and reflux condenser is charged with 600 g of Genapol T-250, and 75 g of glycidyl methacrylate are added. The reaction mixture is then heated at 100° C. for 2 hours, and the excess glycidyl methacrylate is distilled off under reduced pressure. The resulting macromonomer can be used in the polymerization without further purification.

b) Variant 2: Free (Meth)acrylic Acid

A one-liter three-necked flask fitted with stirrer, internal thermometer and reflux condenser is charged with 500 g of Genapol UD-070, and 100 g of (meth)acrylic acid and p-toluenesulfonic acid as catalyst are added. The reaction mixture is then refluxed for 2 hours and the excess acid and the water of reaction which forms are distilled off under reduced pressure. The resulting macromonomer can be used in the polymerization without further purification.

c) Variant 3: Halogen Derivatives of (Meth)acrylic Acid

A one-liter three-necked flask fitted with stirrer, internal thermometer and reflux condenser is charged with 500 g of Genapol UD-070 having a primary amino end-group, and 110 g of (meth)acryloyl chloride and 50 g of sodium carbonate are added. The reaction mixture is then refluxed for 2 hours. The cessation of $CO_2$ evolution indicates the end of the modification reaction. The excess acid chloride is distilled off under reduced pressure. The resulting macromonomer having a (meth)acrylamide end-group can be used in the polymerization without further purification.

d) Variant 4: Esters of (Meth)acrylic Acid

A one-liter three-necked flask fitted with stirrer, internal thermometer and reflux condenser is charged with 500 g of Genapol LA-090, and 100 g of methyl (meth)acrylate and 20 g of titanium tetraisopropoxide are added. The reaction mixture is then refluxed for 2 hours. After the alcohol which forms has been distilled off, the ester which remains is distilled off under reduced pressure. The resulting macromonomer having a (meth)acrylic acid end-group can be used in the polymerization without further purification.

2) Polymerization

General polymerization procedure for preparing the side-chain polymers according to the invention by the precipitation method in t-butanol A 2-liter Quickfit flask fitted with reflux condenser, gas line, internal thermometer and stirrer is charged with 500 ml of t-butanol, and the calculated amount of AMPS is added. The mixture is then neutralized by introducing $NH_3$, and the LCST side arms prepared as under 1) (two or more different species also possible) are added to the reaction mixture. Should further comonomers be required, then these can be added to the reaction mixture after neutralization. After the mixture has been rendered inert with $N_2$ or argon, at an internal temperature of 60° C., AIBN is added as initiator, and the polymerization reaction is started. After a few minutes, precipitation of the prepared polymer results. The mixture is refluxed for two hours, and the polymer is then freed from the solvent using a suction filter and dried under reduced pressure. This procedure can generally be used for all of the polymerization reactions described below.

Side-chain polymers with thickening properties

Example 1

Reaction in Accordance with the General Polymerization Procedure

| Reactant | Amount (g) |
| --- | --- |
| Macromonomer Variant 1 - Genapol ® T-250 type | 20 |
| $NH_3$-neutralized AMPS | 100 |
| t-Butanol | 300 |
| AIBN (initiator) | 1 |

Example 2

Reaction in Accordance with the General Polymerization Procedure

| Reactant | Amount (g) |
| --- | --- |
| Macromonomer Variant 3 - Genapol ® UD-80 type | 30 |
| $NH_3$-neutralized AMPS | 90 |
| t-Butanol | 300 |
| AIBN (initiator) | 1 |

Example 3

Reaction in Accordance with the General Polymerization Procedure

| Reactant | Amount (g) |
| --- | --- |
| Macromonomer Variant 3 - Genapol ® T-250 type | 30 |
| $NH_3$-neutralized AMPS | 90 |
| Methylenebisacrylamide (crosslinker) | 1.5 |
| t-Butanol | 300 |
| AIBN (initiator) | 1 |

Example 4

Reaction in Accordance with the General Polymerization Procedure

| Reactant | Amount (g) |
| --- | --- |
| Macromonomer Variant 1 - Genapol ® L-070 type | 20 |
| Na-neutralized AMPS | 75 |
| Acrylamide | 50 |
| t-Butanol | 300 |
| AIBN (initiator) | 1 |

Example 5

Reaction in Accordance with the General Polymerization Procedure

| Reactant | Amount (g) |
| --- | --- |
| Macromonomer Variant 4 - Genapol ® UD-080 type | 15 |
| Macromonomer Variant 1 - Genapol ® T-250 type | 15 |
| $NH_3$-neutralized AMPS | 100 |
| t-Butanol | 300 |
| AIBN (initiator) | 1 |

Example 6

Reaction in Accordance with the General Polymerization Procedure

| Reactant | Amount (g) |
| --- | --- |
| Macromonomer Variant 1 - Genapol ® LA-110 type | 20 |
| $NH_3$-neutralized AMPS | 100 |
| t-Butanol | 300 |
| AIBN (initiator) | 1 |

Example 7

Reaction in Accordance with the General Polymerization Procedure

| Reactant | Amount (g) |
| --- | --- |
| Macromonomer Variant 1 - Genapol ® T-080 type | 20 |
| $NH_3$-neutralized AMPS | 100 |
| t-Butanol | 300 |
| AIBN (initiator) | 1 |

Example 8

Reaction in Accordance with the General Polymerization Procedure

| Reactant | Amount (g) |
| --- | --- |
| Macromonomer Variant 1 - Genapol ® T-150 type | 25 |
| $NH_3$-neutralized AMPS | 100 |
| AM | 10 |
| t-Butanol | 350 |
| AIBN (initiator) | 1 |

Example 9

Reaction in Accordance with the General Polymerization Procedure

| Reactant | 9.1 Amount (g) | 9.2 Amount (g) | 9.3 Amount (g) |
| --- | --- | --- | --- |
| Macromonomer Variant 1 - Genapol ® LA-110 type | 10 | 20 | 10 |
| Macromonomer Variant 1 - Genapol ® T-150 type | 12.5 | 12.5 | 25 |
| $NH_3$-neutralized AMPS | 100 | 100 | 100 |
| AM | 10 | 10 | 10 |
| t-Butanol | 350 | 350 | 350 |
| AIBN (initiator) | 1 | 1 | 1 |

Example 10

Polymer Mixture

| Polymer | 10.1 Amount (g) | 10.2 Amount (g) | 10.3 Amount (g) |
| --- | --- | --- | --- |
| Example 1 | 10 | 20 | 10 |
| Example 3 | 10 | 10 | 20 |

Example 11

Reaction in Accordance with the General Polymerization Procedure, but at a Starting Temperature of 45° C.

| Reactant | Amount (g) |
| --- | --- |
| Macromonomer Variant 1 - ($C_{18}$—$C_{22}$)-fatty alcohol polyglycol ether with 25 EO units type | 25 |
| $NH_3$-neutralized AMPS | 100 |
| t-Butanol | 300 |
| Azobisdimethylvaleronitrile (initiator) | 1 |

Example 12

Reaction in Accordance with the General Polymerization Procedure, but at a Starting Temperature of 45° C.

| Reactant | Amount (g) |
| --- | --- |
| Macromonomer Variant 1 - Genapol ® UD-080 type | 20 |
| $NH_3$-neutralized AMPS | 100 |
| t-Butanol | 300 |
| Azobisdimethylvaleronitrile (initiator) | 1 |

Example 13

Reaction in Accordance with the General Polymerization Procedure

| Reactant | Amount (g) |
| --- | --- |
| Macromonomer Variant 1 - Genapol ® T-200 type | 15 |
| $NH_3$-neutralized AMPS | 100 |
| t-Butanol | 300 |
| AIBN (initiator) | 1 |

Example 14

Reaction in Accordance with the General Polymerization Procedure

| Reactant | Amount (g) |
| --- | --- |
| Genapol ® T-250 methacrylate | 97 |
| $NH_3$-neutralized AMPS | 3 |
| t-Butanol | 300 |
| TMPTA | 1.8 |
| Dilauroyl peroxide (initiator) | 1 |

Example 15

Reaction in Accordance with the General Polymerization Procedure

| Reactant | Amount (g) |
|---|---|
| MPEG 750 methacrylate | 80 |
| $NH_3$-neutralized AMPS | 20 |
| t-Butanol | 300 |
| TMPTA | 1.8 |
| AIBN (initiator) | 1 |

Viscosity 1.0% strength ($H_2O$ dist.) 55 000 mpas (Brookfield spindle 7)

Viscosity 0.5% strength ($H_2O$ dist.) 19 000 mPas (Brookfield spindle 7)

Example 16

Reaction in Accordance with the General Polymerization Procedure

| Reactant | Amount (g) |
|---|---|
| Genapol ® T-250 methacrylate | 97 |
| $NH_3$-neutralized AMPS | 3 |
| t-Butanol | 300 |
| Dilauroyl peroxide (initiator) | 1 |

Example 17

Reaction in Accordance with the General Polymerization Procedure

| Reactant | Amount (g) |
|---|---|
| MPEG 750 methacrylate | 20 |
| $NH_3$-neutralized AMPS | 80 |
| t-Butanol | 300 |
| ABAH (initiator) | 1 |

Viscosity 1.0% strength ($H_2O$ dist.) 1500 mPas (Brookfield spindle 5)

Viscosity 0.5% strength ($H_2O$ dist.) 400 mPas (Brookfield spindle 5)

Comparative Example 1

Figure 1:
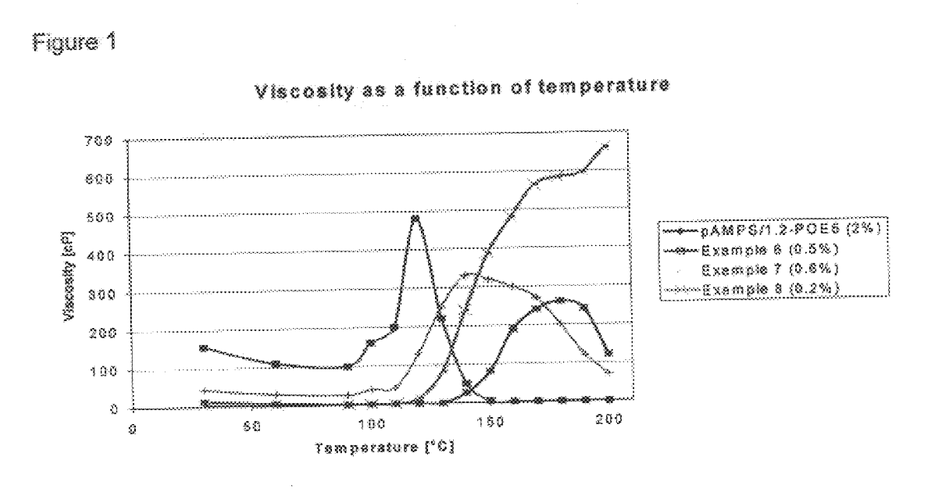
FIG. 1 shows a graph of viscosity as a function of temperature.

Comparative Example 1 shows that the temperature at which viscosification starts and the intensity of the effect can be influenced (FIG. 1). The polymers used are based on Examples 6, 7 and 8. In addition, a polymer from EP-B-0 583 814 is reproduced. This is pAMPS/1.2-POE5 from Example 1.3. FIG. 1 shows the viscosity of the polymers in aqueous solution. FIG. 1 shows that the viscosification maxima are at different temperatures: for Example 6 at 120° C., for Example 7 at 140° C. and for Example 8 at above 200° C. pAMPS/1.2-POE5 has its temperature maximum at 200° C. The use concentrations are, moreover, markedly lower than in the case of pAMPS/1.2-POE5 (FIG. 1).

It is also clear that the polymers according to the invention exhibit a basic viscosity even at room temperature on account of the hydrophobic interaction of the alkyl radicals of the side chains. pAMPS/1.2-POE5 does not form such a basic viscosity. Moreover, the polymers according to the invention are notable for the fact that the breadth of the thermoassociating effect is controllable.

The two examples below show the effect of mixtures of different side arms within a polymer (Example 18), and the effect of mixtures of different polymers (Example 19).

Example 18

Figure 2:
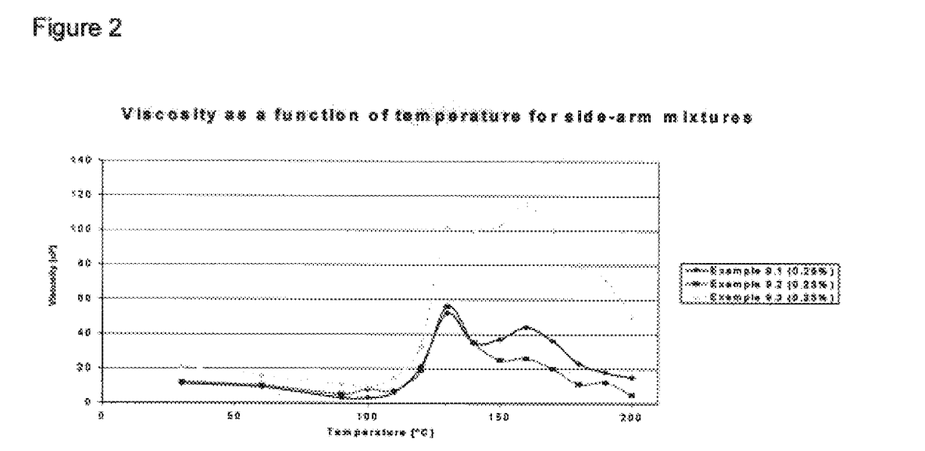
FIG. 2 shows a graph of viscosity as a function of temperature for side-arm mixtures.

This example shows the development of the viscosity at varying temperatures for the polymers from Example 9. Various side arms within a polymer are used (FIG. 2).

Example 19

Figure 3:
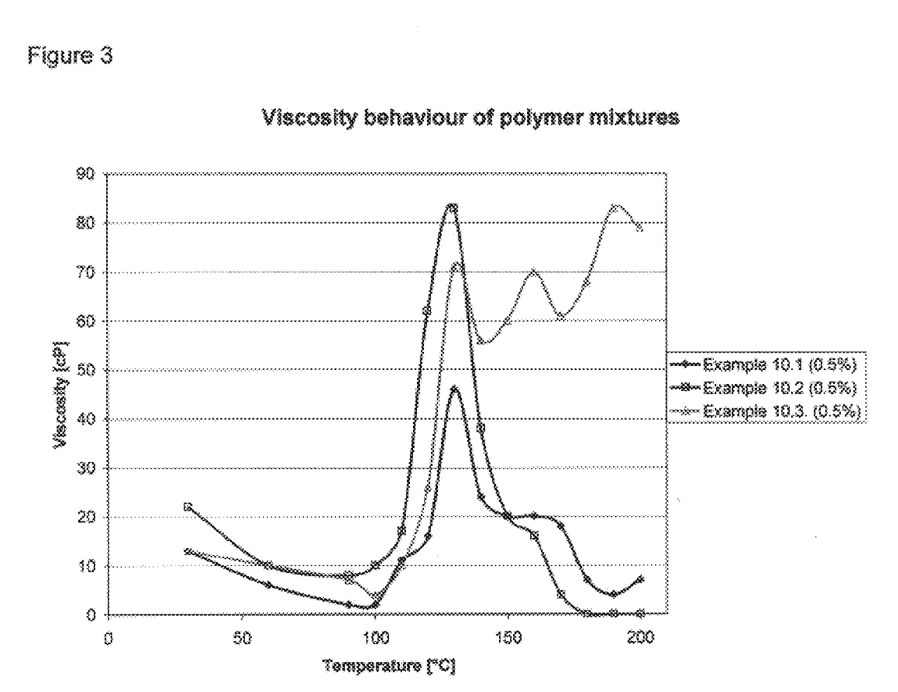
FIG. 3 shows a graph of how the viscosity behavior changes as a function of temperature.

FIG. 3 shows how the viscosity behavior changes as a function of temperature. Examples 10.1 to 10.3 are different mixing ratios of the polymers from Example 6 and Example 7. The breadth and intensity of the thermoassociating effect is adjustable via the mixing ratio.

Examples of Oil Emulsions

The test emulsions are stored at 40° C., 45° C. and 50° C. over a period of 90 days. 3 different oil mixtures are used in each case. The oil mixtures have the following composition:

| Mixture I: | |
|---|---|
| Paraffin oil, low viscosity | 50% |
| Isopropyl palmitate | 30% |
| Soybean oil | 20% |

| Mixture II: | |
|---|---|
| Cetiol V | 25% |
| Squalane | 25% |
| Myritol 318 | 25% |
| Isopropyl palmitate | 25% |

| Mixture III: | |
|---|---|
| Soybean oil | 50% |
| Almond oil | 20% |
| Avocado oil | 20% |
| Jojoba oil | 10% |

Assessment key:

0=no emulsifier effect

1=separated into 2 or 3 phases

3=creaming +oil or water +creaming, homogeneous emulsion inbetween

4=water separation, no creaming, no oil separation

5=oil separation, no creaming, no water separation

6=creaming

7=barely visible creaming

8=virtually in order

9=completely homogeneous emulsion

Emulsifying index:
4.1–5.0=very good
3.1–4.0=good
2.1–3.0=average
1.1–2.0=poor
0–1.0=very poor Test emulsions containing noncrosslinked polymers according to the invention

| Composition | 20 | 21 | 22 | 23 | 24 | 25 | 26 | 27 | 28 | 29 | 30 | 31 |
|---|---|---|---|---|---|---|---|---|---|---|---|---|
| Polymer as in Ex. 2 | — | — | — | 1.0 | — | — | 1.0 | — | — | 0.5 | — | — |
| Polymer as in Ex. 1 | — | 1.0 | 1.0 | — | — | 1.0 | — | — | 1.0 | — | — | 0.5 |
| Polymer as in Ex. 6 | 1.0 | — | — | — | 1.0 | — | — | 1.0 | — | — | 0.5 | — |
| Oil mixture I | 19.0 | 19.0 | — | — | — | — | — | — | — | — | — | — |
| Oil mixture II | — | — | 19.0 | — | — | — | — | — | — | — | — | — |
| Oil mixture III | — | — | — | 19.0 | 19.0 | 19.0 | 27.0 | 27.0 | 27.0 | 27.0 | 27.0 | 27.0 |
| Carbopol 980 | 0.3 | 0.3 | 0.3 | 0.3 | 0.3 | 0.3 | — | — | — | — | — | — |
| Sodium hydroxide solution 10% strength | 1.2 | 1.2 | 1.2 | 1.2 | 1.2 | 1.2 | — | — | — | — | — | — |
| Water | ad 100 | ad 100 | ad 100 | ad 100 | ad 100 | ad 100 | ad 100 | ad 100 | ad 100 | ad 100 | ad 100 | ad 100 |
| Emulsifying index | 3.9 | 4.0 | 4.0 | 3.9 | 3.8 | 3.7 | 2.8 | 2.5 | 2.8 | 2.8 | 2.6 | 2.7 |
| Emulsifying effect | good | good | good | good | good | good | moderate | moderate | moderate | moderate | moderate | moderate |

The stability test shows that the noncrosslinked polymers according to the invention in combination with additional bodying agent produce stable emulsions.

Test emulsions containing crosslinked polymers according to the invention

| Composition | 32 | 33 | 34 | 35 | 36 | 37 | 38 | 39 | 40 |
|---|---|---|---|---|---|---|---|---|---|
| Polymer as in Ex. 3 | 1 | 1 | 1 | 1 | 1 | 1 | 0.75 | 0.75 | 0.75 |
| Oil mixture I | 27 | | | 27 | | | 27 | | |
| Oil mixture II | | 27 | | | 27 | | | 27 | |
| Oil mixture III | | | 27 | | | 27 | | | 27 |
| Carbopol 980 | 0.3 | 0.3 | 0.3 | — | — | — | — | — | — |
| Sodium hydroxide solution 10% strength | 1.2 | 1.2 | 1.2 | — | — | — | — | — | — |
| Water | ad 100 | ad 100 | ad 100 | ad 100 | ad 100 | ad 100 | ad 100 | ad 100 | ad 100 |
| Emulsifying index | 4.7 | 4.8 | 4.7 | 4.6 | 4.4 | 4.5 | 4.5 | 4.6 | 4.6 |
| Emulsifying effect | very good | very good | very good | very good | very good | very good | very good | very good | very good |

The stability test shows that the crosslinked polymers according to the invention act both as a bodying agent and as an emulsifier with very good emulsifying properties. Stable emulsions are obtained without additional coemulsifier and without additional bodying agents.

Formulation examples, all data in % by weight

Example 41

O/W Skin Milk

| | Composition: | |
|---|---|---|
| A | Polymer as in Ex. 2 | 0.50% |
| | Mineral oil, low viscosity | 5.00% |
| | ® Miglyol 812 (Dynamit Nobel) Caprylic/capric triglycerides | 4.00% |

-continued

|   |   |   |
|---|---|---|
|   | Isopropyl palmitate | 6.00% |
|   | Soybean oil | 3.00% |
|   | Jojoba oil | 2.00% |
| B | ® Aristoflex AVC (Clariant) AMPS/VIFA copolymer | 30% |
| C | ® Hostapon KCG (Clariant) Sodium cocoyl glutamate | 1.00% |
|   | Water | ad 100% |
|   | Glycerol | 3.00% |
|   | Sodium hydroxide (10% in water) | 1.20% |
| D | Fragrances | 0.30% |
|   | Preparation |   |
| I | Stir B into A, add C and stir well |   |
| II | Stir D into I |   |
| III | Homogenize the emulsion |   |

Example 42

O/W Skin Milk

|   |   |   |
|---|---|---|
|   | Composition |   |
| A | Polymer as in Ex. 1 | 0.50% |
|   | Isopropyl palmitate | 4.00% |
|   | Almond oil | 4.00% |
|   | Wheatgerm oil | 1.00% |
|   | ® Cetiol SN (Henkel) Cetearyl isononanoate | 8.00% |
| B | ® Aristoflex AVC (Clariant) AMPS/VIFA copolymer | 0.30% |
| C | Water | ad 100% |
| D | Fragrances | 0.30% |
|   | Preparation |   |
| I | Mix A and B, then add C |   |
| II | Stir D into I |   |
| III | Homogenize the emulsion |   |

Example 43

O/W Aftersun Milk

|   |   |   |
|---|---|---|
|   | Composition: |   |
| A | Polymer as in Ex. 1 | 1.00% |
|   | Isopropyl palmitate | 5.00% |
|   | ® Cetiol SN (Henkel) Cetearyl isononanoate | 4.00% |
|   | Soybean oil | 4.00% |
|   | ® Miglyol 812 (Dynamit Nobel) Caprylic/capric triglycerides | 3.00% |
|   | Jojoba oil | 3.00% |
|   | Wheatgerm oil | 1.00% |
| D | ® AQUAMOLLIN BC powder, high-conc. (Clariant) Ethylenediaminetetraacetic acid sodium salt | 0.10% |
|   | Citric acid (10% strength) | 0.30% |
|   | Water | 68.80% |
|   | Glycerol | 3.00% |
|   | ALLANTOIN (Clariant) | 0.20% |
|   | Preservative | q.s. |
| E | Ethanol | 1.50% |
|   | Perfume oil | 0.30% |

-continued

|   |   |
|---|---|
| Preparation |   |
| I | Stir the components of A until homogeneous |
| II | At about 35° C., stir D into I |
| III | Homogenize the emulsion |

Examples of Water-in-oil Formulations

Example 44

Reaction According to the General Polymerization Procedure

| Reactant | Amount (g) |
|---|---|
| Genapol ® T-250 methacrylate | 90 |
| NH₃-neutralized AMPS | 10 |
| TMPTA | 1.5 |
| t-Butanol | 300 |
| Dilauroyl peroxide (initiator) | 1 |

Example 45

W/O Cream

|   |   |   |
|---|---|---|
|   | Composition |   |
| A | ® HOSTACERIN DGI (Clariant) Polyglyceryl-2 Sesquiisostearate | 4.00% |
|   | Beeswax | 2.00% |
|   | Polymer as in Ex. 18 | 1.5% |
|   | Mineral oil, low viscosity | 5.00% |
|   | Vaseline | 10.00% |
|   | ® Cetiol V (Henkel KGaA) Decyl Oleate | 5.00% |
| B | 1,2-Propylene glycol | 3.00% |
|   | Water | 69.10% |
|   | Preservative | q.s. |
| C | Fragrance | 0.40% |
|   | Preparation |   |
| I | Melt A at 80° C. |   |
| II | Heat B to 80° C. |   |
| III | Stir II into I |   |
| IV | Stir until cool |   |
| V | At 35° C. add C to IV |   |

Examples of Surfactant Formulations

Example 46

Body Wash

|   |   |   |
|---|---|---|
|   | Composition |   |
| A | ® GENAPOL LRO liquid (Clariant) Sodium Laureth Sulfate | 40.00% |
| B | Fragrance | 0.30% |
| C | Water | 52.70% |
|   | Dye | q.s. |
|   | Preservative | q.s. |

-continued

| | | |
|---|---|---|
| | ® GENAGEN LDA (Clariant) | 6.00% |
| | Disodium Lauroamphodiacetate | |
| | Citric Acid | q.s. |
| D | Polymer as in Ex. 6 | 1.00% |
| | Preparation | |
| I | Stir B into A | |
| II | Add components of C one after the other to I | |
| III | Adjust the pH to 5.5 | |
| IV | Adjust the viscosity by stirring D into II | |

Example 47

Baby Shampoo

| | Composition | |
|---|---|---|
| A | Water | 60.70% |
| | ® GENAPOL ZRO liquid (Clariant) | 25.00% |
| | Sodium Laureth Sulfate | |
| | ® HOSTAPON CLG (Clariant) | 8.00% |
| | Sodium Lauroyl Glutamate | |
| | ® GENAPOL SBE (Clariant) | 5.00% |
| | Disodium Laureth Sulfosuccinate | |
| | Fragrance | 0.30% |
| | Dye solution | q.s. |
| | Preservative | q.s. |
| B | Polymer as in Example 4 | 1.00% |
| | Preparation | |
| I | Dissolve B in A | |
| II | If necessary, adjust the pH | |

Example 48

Antidandruff Shampoo, Clear

| | Composition | |
|---|---|---|
| A | ® OCTOPIROX (Clariant) | 0.50% |
| | Piroctone Olamine | |
| B | Water | 10.00% |
| C | ® GENAPOL LRO LIQUID (Clariant) | 30.00% |
| | Sodium Laureth Sulfate | |
| D | ® Belsil DMC 6032 (Wacker Chemie) | 1.50% |
| | Dimethicone Copolyol Acetate | |
| | Fragrance | 0.30% |
| E | ® ALLANTOIN (Clariant) | 0.30% |
| F | Water | 46.40% |
| G | Dye solution | q.s. |
| | Panthenol (Hoffmann La Roche) | 1.00% |
| | ® GENAGEN CAB (Clariant) | 8.00% |
| | Cocamidopropyl Betaine | |
| H | Polymer as in Example 7 | 1.10% |
| | Preparation | |
| I | Mix A with B | |
| II | Stir C into I until a clear solution forms | |
| III | Add components of D one after the other to I | |
| IV | Stir E into F with warming and then stir into I | |
| V | Add components of G one after the other to I | |
| VI | If necessary adjust the pH | |
| VII | Adjust the viscosity by stirring H into I | |

Example 49

Antidandruff Shampoo, Pearlescent

| | Composition | |
|---|---|---|
| A | Water | 38.7% |
| B | ® HOSTAPON SCI-65 (Clariant) | 3.00% |
| | Sodium Cocoyl Isethionate | |
| C | ® GENAPOL LRO liquid (Clariant) | 35.00% |
| | Sodium Laureth Sulfate | |
| | ® HOSTAPON KCG (Clariant) | 5.00% |
| | Sodium Cocoyl Glutamate | |
| | ® Belsil DMC 6032 (Wacker) | 1.00% |
| | Dimethicone Copolyol Acetate | |
| | Fragrance | 0.30% |
| | ® GENAGEN CAB (Clariant) | 9.00% |
| | Cocamidopropyl Betaine | |
| | GENAPOL TSM (Clariant) | 4.00% |
| | PEG-3 Distearate (and) Sodium Laureth Sulfate | |
| | Merquat 550 | 0.50% |
| | Polyquaternium-7 | |
| | Zinc Omadine FPS (Olin) | |
| | Zinc Pyrithione (48% strength) | 2.50% |
| | Polymer as in Ex. 9.1 | 1.00% |
| | Dye solution | q.s. |
| | Preservative | q.s. |
| | Preparation | |
| I | At 80° C., dissolve B in A | |
| II | After cooling to about 35° C., add components C one after the other | |

Examples of Gels

Example 50

Hair Gel with Conditioning Properties

| | Composition | |
|---|---|---|
| A | Water | 92.00% |
| | Panthenol | 1.50% |
| | UVAsorb S5 | 0.05% |
| | Benzophenone-4 | |
| | Dye solution | q.s. |
| | Preservative | q.s. |
| B | ® Emulsogen HCO 040 (Clariant) | 0.50% |
| | PEG-40 Hydrogenated Castor Oil | |
| | Perfume | q.s. |
| C | Polymer as in Example 3 | 2.00% |
| D | Gafquat 755N (ISP) | 2.50% |
| | Polyquaternium-11 | |
| | Preparation | |
| I | Mix components A | |
| II | Mix components B and add to I | |
| III | Add C to D to I | |

Example 51

Hair Gel with Strong Hold

| | Composition | |
|---|---|---|
| A | Water | 91.50% |
| | PVP K-30 (ISP) | 4.00% |
| | PVP | |
| | Panthenol | 0.50% |

-continued

|   | | |
|---|---|---|
|   | UVAsorb S5 | 0.05% |
|   | Benzophenone-4 | |
|   | Dye solution | q.s. |
|   | Preservative | q.s. |
| B | Abil B 8851 (Goldschmidt) | 1.00% |
|   | Dimethicone Copolyol | |
|   | ® Emulsogen HCO 040 (Clariant) | 0.50% |
|   | PEG-40 Hydrogenated Castor Oil | |
|   | Perfume | q.s. |
| C | Polymer as in Example 3 | 2.50% |
|   | Preparation | |
| I | Mix components A | |
| II | Add components B to I | |
| III | Add components C to I | |

What is claimed is:

1. A water-soluble polyimier preparable by free-radical copolymerization of
   A) one or more macromonomers containing an end-group capable of polymerization, a hydrophilic moiety based on polyalkylene oxides, and a hydrophobic moiety which comprises hydrogen or a saturated or unsaturated, linear or branched, aliphatic, cycloaliphatic or aromatic $(C_1–C_{30})$-hydrocarbon radical, wherein the macromonomers have a proportion of 50.1 to 99.9 mol % of the polymer, and
   B) one or more olefincally unsaturated comonomers wherein the comonomers are styrenesulfonic acid, acrylamidopropylmethylenesulfonic acid (AMPS), vinylsulfonic acid, vinylphosphonic acid, allylsulfonic acid, methallylsulfonic acid and salts thereof; esters of (meth)acrylic acid with aliphatic, aromatic or cycloaliphatic alcohols having a carbon number from 1 to 22; esters of (meth)acrylic acid with alkyl ethoxylates, open-chain and cyclic N-vinylamides (N-vinyllactams) having a ring size of from 4 to 9 atoms; N,N-dimethylacrylamide, N,N-diethylacrylamide, alkoxylated acrylamides and methacrylamides; 2-vinylpyridine; 4-vinylpyridine; vinyl acetate; glycidyl methacrylate; acrylonitrile, vinyl chloride; vinylidene chloride; tetrafluoroethylene and/or diallyldimethylammonium chloride (DADMAC).

2. The polymer as claimed in claim 1, wherein the macromonomers A) are those of the formula (1)

$$R^1{-}Y{-}(R^2{-}O)_x{-}R^3 \qquad (1)$$

in which $R^1$ is a vinyl, allyl, acrylic or methacrylic radical; $R^2$ is $(C_2–C_4)$-alkylene; x is an integer between 1 and 500; Y=O, S, PH or NH; and $R^3$ is hydrogen or a saturated or unsaturated linear or branched aliphatic, cycloaliphatic or aromatic $(C_1–C_{30})$-hydrocarbon radical.

3. The polymer as claimed in claim 1, wherein the comonomers B) are olefinically unsaturated acids and/or salts thereof containing mono- and divalent counterions.

4. The polymer as claimed in claim 3, wherein the comonomers B) are acrylamidopropylmethylenesulfonic acid (AMPS); esters of (meth)acrylic acid with aliphatic, aromatic or cycloaliphatic alcohols having a carbon number from 1 to 22; esters of (meth)acrylic acid with alkyl ethoxylates, open-chain and cyclic N-vinylamides having a ring size of from 4 to 9 atoms; 2-vinylpyridine; 4-vinylpyridine; vinyl acetate; glycidyl methacrylate; acrylonitrile; vinyl chloride; vinylidene chloride; tetrafluoroethylene and/or diallyldimethylammonium chloride (DADMAC).

5. The polymer as claimed in claim 1, preparable by free-radical copolymerization of
   A) one or more macromonomers chosen from the group of esters of (meth)acrylic acid with alkyl ethoxylates which include 5 to 80 ethylene oxide (EO) units and $(C_{10}–C_{22})$-alkyl radicals, and
   B) one or more olefinically unsaturated comonomers chosen from the group consisting of acrylamidopropylmethylenesulfonic acid (AMPS), sodium and ammonium salts of acrylamidopropylmethylenesulfonic acid (AMPS), N-vinylformamide, N-vinylmethylacetamide and sodium methallylsulfonate.

6. The polymer as claimed in claim 1, which has been crosslinked by copolymerization of at least one crosslinker having at least two unsaturated double bonds.

7. The polymer as claimed in claim 1, which consists of a water-soluble polymer skeleton and macromonomers A) having heat-sensitive side chains, which have lower critical solution temperature (LCST) behavior in water, and the aqueous solution of which has a viscosity which, above a certain threshold temperature, increases or remains roughly constant with increasing temperature.

8. The polymer as claimed in claim 1, wherein the aqueous solution thereof has a viscosity which, below a first threshold temperature, is low, above this first threshold temperature increases to a maximum with increasing temperature, and above a second threshold temperature decreases again with increasing temperature.

9. The polymer as claimed in claim 1, wherein its 1% strength aqueous solution at room temperature exhibits a viscosity of from 20,000 mPas to 100,000 mPas, and the solution does not exhibit thermoassociative behavior.

10. The polymer as claimed in claim 1, which is prepared by precipitation polymerization in tert-butanol.

11. The polymer as claimed in claim 1, wherein at least one comonomer B) is acrylamidopropylmethylenesulfonic acid (AMPS) or its salts.

12. A water-soluble polymer preparable by free-radical copolymerization of
    A) one or more macromonomers containing an end-group capable of polymerization, a hydrophilic moiety based on polyalkylene oxides, and a hydrophobic moiety which comprises hydrogen or a saturated or unsaturated, linear or branched, aliphatic, cycloaliphatic or aromatic $(C_1–C_{30})$-hydrocarbon radical, wherein the macromonomers are in a proportion of 0.1 to 50 mol %, and
    B) one or more olefinically unsaturated comonomers wherein the comonomers are styrenesulfonic acid, acrylamidopropylmethylenesulfonic acid (AMPS), vinylsulfonic acid, vinylphosphonic acid, allylsulfonic acid, methallylsulfonic acid and salts thereof; esters of (meth)acrylic acid with aliphatic, aromatic or cycloaliphatic alcohols having a carbon number from 1 to 22; esters of (meth)acrylic acid with alkyl ethoxylates, open-chain and cyclic N-vinylamides (N-vinyllactams) having a ring size of from 4 to 9 atoms; N,N-dimethylacrylamide, N,N-diethylacrylamide, alkoxylated acrylamides and methacrylamides; 2-vinylpyridine; 4-vinylpyridine; vinyl acetate; glycidyl methacrylate, acrylonitrile; vinyl chloride; vinylidene chloride; tetrafluoroethylene and/or diallyldimethylammonium chloride (DADMAC).

13. The polymer as claimed in claim 12, wherein the macromonomers A) are those of the formula (1)

$$R^1{-}Y{-}(R^2{-}O)_x{-}R^3 \qquad (1)$$

in which R¹ is a vinyl, allyl, acrylic or methacrylic radical; R² is (C₂–C₄)-alkylene; x is an integer between 1 and 500; Y=O, S, PH or NH; and R³ is hydrogen or a saturated or unsaturated linear or branched aliphatic, cycloaliphatic or aromatic (C₁–C₃₀)-hydrocarbon radical.

14. The polymer as claimed in claim 12, wherein the comonomers B) are olefinically unsaturated acids and/or salts thereof containing mono- and divalent counterions.

15. The polymer as claimed in claim 14, wherein the comonomers B) are acrylamidopropylmethylenesulfonic acid (AMPS); esters of (meth)acrylic acid with aliphatic, aromatic or cycloaliphatic alcohols having a carbon number from 1 to 22; esters of (meth)acrylic acid with alkyl ethoxylates, open-chain and cyclic N-vinylamides having a ring size of from 4 to 9 atoms; 2-vinylpyridine; 4-vinylpyridine; vinyl acetate; glycidyl methacrylate; acrylonitrile; vinyl chloride; vinylidene chloride; tetrafluoroethylene and/or diallyldimethylammonium chloride (DADMAC).

16. The polymer as claimed in claim 12, preparable by free-radical copolymerization of
A) one or more macromonomers chosen from the group of esters of (meth)acrylic acid with alkyl ethoxylates which include 5 to 80 ethylene oxide (EO) units and (C₁₀–C₂₂)-alkyl radicals, and
B) one or more olefinically unsaturated comonomers chosen from the group consisting of acrylamidopropylmethylenesulfonic acid (AMPS), sodium and ammonium salts of acrylamidopropylmethylenesulfonic acid (AMPS), N-vinylformamide, N-vinylmethylacetamide and sodium methallylsulfonate.

17. The polymer as claimed in claim 12, which has been crosslinked by copolymerization of at least one crosslinker having at least two unsaturated double bonds.

18. The polymer as claimed in claim 12, which consists of a water-soluble polymer skeleton and macromonomers A) having heat-sensitive side chains, which have lower critical solution temperature (LCST) behavior in water, and the aqueous solution of which has a viscosity which, above a certain threshold temperature, increases or remains roughly constant with increasing temperature.

19. The polymer as claimed in claim 12, wherein the aqueous solution thereof has a viscosity which, below a first threshold temperature, is low, above this first threshold temperature increases to a maximum with increasing temperature, and above a second threshold temperature decreases again with increasing temperature.

20. The polymer as claimed in claim 12, wherein its 1% strength aqueous solution at room temperature exhibits a viscosity of from 20,000 mPas to 100,000 mPas, and the solution does not exhibit thermoassociative behavior.

21. The polymer as claimed in claim 12, which is prepared by precipitation polymerization in tert-butanol.

22. The polymer as claimed in claim 12, wherein at least one comonomer B) is acrylamidopropylmethylenesulfonic acid (AMPS) or its salts.

23. A water-soluble polymer preparable by free-radical copolymerization of
A) one or more macromonomers containing an end-group capable of polymerzation, a hydrophilic moiety based on polyalkylene oxides, and a hydrophobic moiety which comprises hydrogen or a saturated or unsaturated, linear or branched, aliphatic, cycloaliphatic or aromatic (C₁–C₃₀)-hydrocarbon radical, and
B) one or more olefinically unsaturated comonomers wherein the comonomers are styrenesulfonic acid, acrylamidopropylmethylenesulfonic acid (AMPS), vinylsulfonic acid, vinylphosphonic acid, allylsulfonic acid, methallylsulfonic acid and salts thereof; esters of (meth)acrylic acid with aliphatic, aromatic or cycloaliphatic alcohols having a carbon number from 1 to 22; esters of (meth)acrylic acid with alkyl ethoxylates, open-chain and cyclic N-vinylamides (N-vinyllactams) having a ring size of from 4 to 9 atoms; N,N-dimethylacrylamide, N,N-diethylacrylamide, alkoxylated acrylamides and methacrylamides; 2-vinylpyridine; 4-vinylpyridine; vinyl acetate; glycidyl methacrylate; acrylonitrile; vinyl chloride; vinylidene chloride; tetrafluoroethylene and/or diallyldimethylammonium chloride (DADMAC); wherein its 1% strength aqueous solution at room temperature exhibits a viscosity of from 20,000 mPas to 100,000 mPas, and the solution does not exhibit thermoassociative behavior.

24. The polymer as claimed in claim 23, wherein the macromonomers A) are those of the formula (1)

$$R^1—Y—(R^2—O)_x—R^3 \qquad (1)$$

in which R¹ is a vinyl, allyl, acrylic or methacrylic radical; R² is (C₂–C₄)-alkylene; x is an integer between 1 and 500; Y=O, S, PH or NH; and R³ is hydrogen or a saturated or unsaturated linear or branched aliphatic, cycloaliphatic or aromatic (C₁–C₃₀)-hydrocarbon radical.

25. The polymer as claimed in claim 23, wherein the comonomers B) are olefinically unsaturated acids and/or salts thereof containing mono- and divalent counterions.

26. The polymer as claimed in claim 25, wherein the comonomers B) are acrylamidopropylmethylenesulfonic acid (AMPS); esters of (meth)acrylic acid with aliphatic, aromatic or cycloaliphatic alcohols having a carbon number from 1 to 22; esters of (meth)acrylic acid with alkyl ethoxylates, open-chain and cyclic N-vinylamides having a ring size of from 4 to 9 atoms; 2-vinylpyridine; 4-vinylpyridine; vinyl acetate; glycidyl methacrylate; acrylonitrile; vinyl chloride; vinylidene chloride; tetrafluoroethylene and/or diallyldimethylammonium chloride (DADMAC).

27. The polymer as claimed in claim 23, preparable by free-radical copolymerization of
A) one or more macromonomers chosen from the group of esters of (meth)acrylic acid with alkyl ethoxylates which include 5 to 80 ethylene oxide (EO) units and (C₁₀–C₂₂)-alkyl radicals, and
B) one or more olefinically unsaturated comonomers chosen from the group consisting of acrylamidopropylmethylenesulfonic acid (AMPS), sodium and ammonium salts of acrylamidopropylmethylenesulfonic acid (AMPS), N-vinylformamide, N-vinylmethylacetamide and sodium methallylsulfonate.

28. The polymer as claimed in claim 23, wherein the macromonomers are in a proportion 50.1 to 99.9 mol %.

29. The polymer as claimed in claim 23, wherein the macromonomers are in a proportion of 0.1 to 50 mol %.

30. The polymer as claimed in claim 23, which has been crosslinked by copolymerization of at least one crosslinker having at least two unsaturated double bonds.

31. The polymer as claimed in claim 23, which consists of a water-soluble polymer skeleton and macromonomers A) having heat-sensitive side chains, which have lower critical solution temperature (LCST) behavior in water, and the aqueous solution of which has a viscosity which, above a certain threshold temperature, increases or remains roughly constant with increasing temperature.

32. The polymer as claimed in claim 23, wherein the aqueous solution thereof has a viscosity which, below a first threshold temperature, is low, above this first threshold temperature increases to a maximum with increasing temperature, and above a second threshold temperature decreases again with increasing temperature.

33. The polymer as claimed in claim 23, which is prepared by precipitation polymerization in tert-butanol.

34. A water-soluble polymer preparable by free-radical copolymerization of

A) one or more macromonomers containing an end-group capable of polymerization, a hydrophilic moiety based on polyalkylene oxides, and a hydrophobic moiety which comprises hydrogen or a saturated or unsaturated, linear or branched, aliphatic, cycloaliphatic or aromatic ($C_1$–$C_{30}$)-hydrocarbon radical, and B) one or more olefinically unsaturated comonomers wherein the comonomers are styrenesulfonic acid, acrylamidopropylmethylenesulfonic acid (AMPS), vinylsulfonic acid, vinylphosphonic acid, allylsulfonic acid, methallylsulfonic acid and salts thereof; esters of (meth)acrylic acid with aliphatic, aromatic or cycloaliphatic alcohols having a carbon number from 1 to 22; esters of (meth)acrylic acid with alkyl ethoxylates, open-chain and cyclic N-vinylamides (N-vinyllactams) having a ring size of from 4 to 9 atoms; N,N-dimethylacrylamide, N,N-diethylacrylamide, alkoxylated acrylamides and methacrylamides; 2-vinylpyridine; 4-vinylpyridine; vinyl acetate; glycidyl methacrylate; acrylonitrile; vinyl chloride; vinylidene chloride; tetrafluoroethylene and/or diallyldimethylammonium chloride (DADMAC);

which is prepared by precipitation polymerization in tert-butanol.

35. The polymer as claimed in claim 34, wherein the macromonomers A) are those of the formula (1)

$$R^1\text{—}Y\text{—}(R^2\text{—}O)_x\text{—}R^3 \quad (1)$$

in which $R^1$ is a vinyl, allyl, acrylic or methacrylic radical; $R^2$ is ($C_2$–$C_4$)-alkylene; x is an integer between 1 and 500; Y=O, S, PH or NH; and $R^3$ is hydrogen or a saturated or unsaturated linear or branched aliphatic, cycloaliphatic or aromatic ($C_1$–$C_{30}$)-hydrocarbon radical.

36. The polymer as claimed in claim 34, wherein the comonomers B) are olefinically unsaturated acids and/or salts thereof containing mono- and divalent counterions.

37. The polymer as claimed in claim 36, wherein the comonomers B) are acrylamidopropylmethylenesulfonic acid (AMPS); esters of (meth)acrylic acid with aliphatic, aromatic or cycloaliphatic alcohols having a carbon number from 1 to 22; esters of (meth)acrylic acid with alkyl ethoxylates, open-chain and cyclic N-vinylamides having a ring size of from 4 to 9 atoms; 2-vinylpyridine; 4-vinylpyridine; vinyl acetate; glycidyl methacrylate; acrylonitrile; vinyl chloride; vinylidene chloride; tetrafluoroethylene and/or diallyldimethylammonium chloride (DADMAC).

38. The polymer as claimed in claim 34, preparable by free-radical copolymerization of A) one or more macromonomers chosen from the group of esters of (meth)acrylic acid with alkyl ethoxylates which include 5 to 80 ethylene oxide (EO) units and ($C_{10}$–$C_{22}$)-alkyl radicals, and B) one or more olefinically unsaturated comonomers chosen from the group consisting of acrylamidopropylmethylenesulfonic acid (AMPS), sodium and ammonium salts of acrylamidopropylmethylenesulfonic acid (AMPS), N-vinylformamide, N-vinylmethylacetamide and sodium methallylsulfonate.

39. The polymer as claimed in claim 34, wherein the macromonomers are in a proportion of 50.1 to 99.9 mol %.

40. The polymer as claimed in claim 34, wherein the macromonomers are in a proportion of 0.1 to 50 mol %.

41. The polymer as claimed in claim 34, which has been crosslinked by copolymerization of at least one crosslinker having at least two unsaturated double bonds.

42. The polymer as claimed in claim 34, which consists of a water-soluble polymer skeleton and macromonomers A) having heat-sensitive side chains, which have lower critical solution temperature (LCST) behavior in water, and the aqueous solution of which has a viscosity which, above a certain threshold temperature, increases or remains roughly constant with increasing temperature.

43. The polymer as claimed in claim 34, wherein the aqueous solution thereof has a viscosity which, below a first threshold temperature, is low, above this first threshold temperature increases to a maximum with increasing temperature, and above a second threshold temperature decreases again with increasing temperature.

44. The polymer as claimed in claim 34, wherein its 1% strength aqueous solution at room temperature exhibits a viscosity of from 20,000 mPas to 100,000 mPas, and the solution does not exhibit thermoassociative behavior.

45. An aqueous preparation, aqueous-alcoholic preparation, aqueous/surface-active preparation, emulsion or suspension comprising polymers as claimed in claim 1.

46. An aqueous preparation, aqueous-alcoholic preparation, aqueous/surface-active preparation, emulsion or suspension comprising polymers as claimed in claim 12.

47. An aqueous preparation, aqueous-alcoholic preparation, aqueous/surface-active preparation, emulsion or suspension comprising polymers as claimed in claim 23.

48. An aqueous preparation, aqueous-alcoholic preparation, aqueous/surface-active preparation, emulsion or suspension comprising polymers as claimed in claim 34.

49. The preparation, emulsion or suspension as claimed in claim 45, which is a cosmetic or pharmaceutical composition.

50. The preparation, emulsion or suspension as claimed in claim 46, which is a cosmetic or pharmaceutical composition.

51. The preparation, emulsion or suspension as claimed in claim 47, which is a cosmetic or pharmaceutical composition.

52. The preparation, emulsion or suspension as claimed in claim 48, which is a cosmetic or pharmaceutical composition.

53. The preparation, emulsion or suspension as claimed in claim 45, which, based on the finished formulation, comprises 0.05 to 10% by weight of polymers.

54. The preparation, emulsion or suspension as claimed in claim 46, which, based on the finished formulation, comprises 0.05 to 10% by weight of polymers.

55. The preparation, emulsion or suspension as claimed in claim 47, which, based on the finished formulation, comprises 0.05 to 10% by weight of polymers.

56. The preparation, emulsion or suspension as claimed in claim 48, which, based on the finished formulation, comprises 0.05 to 10% by weight of polymers.

57. A method of fusing the polymer as claimed in claim 1, the method comprising adding the polymer as a thickener, dispersing agent, suspending agent, emulsifier, stabilizer and/or bodying agent to an emulsion.

58. A method of using the polymer as claimed in claim 12, the method comprising adding the polymer as a thickener, dispersing agent, suspending agent, emulsifier, stabilizer and/or bodying agent to an emulsion.

59. A method of using the polymer as claimed in claim 23, the method comprising adding the polymer as a thickener, dispersing agent, suspending agent, emulsifier, stabilizer and/or bodying agent to an emulsion.

60. A method of using the polymer as claimed in claim 34, the method comprising adding the polymer as a thickener, dispersing agent, suspending agent, emulsifier, stabilizer and/or bodying agent to an emulsion.

61. A method of using the polymer as claimed in claim 1, the method comprising adding the polymer to a crop protection formulation.

62. A method of using the polymer as claimed in claim 12, the method comprising adding the polymer to a crop protection formulation.

63. A method of using the polymer as claimed in claim 23, thee method comprising adding the polymer to a crop protection formulation.

64. A method of using the polymer as claimed in claim 34, the method comprising adding the polymer to a crop protection formulation.

65. A crop protection formulation comprising the polymer as claimed in claim 1.

66. A crop protection formulation comprising the polymer as claimed in claim 12.

67. A crop protection formulation comprising the polymer as claimed in claim 23.

68. A crop protection formulation comprising the polymer as claimed in claim 34.

69. The polymer as claimed in claim 1, wherein the N-vinylamides (N-vinyllactams) having a ring size of from 4 to 9 atoms are selected from the group consisting of N-vinylformamide (NVF), N-vinylmethylformamide, N-vinylmethylacetamide (VIMA), N-vinylacetamide and N-vinylcaprolactam.

70. The polymer as claimed in claim 1, wherein the acrylamides are methacryloyl propyl trimethyl ammonium chloride (MAPTAC) and acryloyl propyl trimethyl ammonium chloride (APTAC).

71. The polymer as claimed in claim 12, wherein the N-vinylamides (N-vinyllactams) having a ring size of from 4 to 9 atoms are selected from the group consisting of N-vinylformamide (NVF), N-vinylmethylformamide, N-vinylmethylacetamide (VIMA), N-vinylacetamide and N-vinylcaprolactam.

72. The polymer as claimed in claim 12, wherein the acrylamides are methacryloyl propyl trimethyl ammonium chloride (MAPTAC) and acryloyl propyl trimethyl ammonium chloride (APTAC).

73. The polymer as claimed in claim 23, wherein the N-vinylamides (N-vinyllactams) having a ring size of from 4 to 9 atoms are selected from the group consisting of N-vinylformamide (NVF), N-vinylmethylformamide, N-vinylmethylacetamide (VIMA), N-vinylacetamide and N-vinylcaprolactam.

74. The polymer as claimed in claim 23, wherein the acrylamides are methacyloyl propyl trimethyl ammonium chloride (MAPTAC) and acryloyl propyl trimethyl ammonium chloride (APTAC).

75. The polymer as claimed in claim 34, wherein the N-vinylamides (N-vinyllactams) having a ring size of from 4 to 9 atoms are selected from the group consisting of N-vinylformamide (NVF), N-vinylmethylformamide, N-vinylmethylacetamide (VIMA), N-vinylacetamide and N-vinylcaprolactam.

76. The polymer as claimed in claim 34, wherein the acrylamides are methacryloyl propyl trimethyl ammonium chloride (MAPTAC) and acryloyl propyl trimethyl ammonium chloride (APTAC).

\* \* \* \* \*